United States Patent [19]
Surinx

[11] 3,946,594
[45] Mar. 30, 1976

[54] DISPOSABLE PHASE CHANGE DEVICE

[75] Inventor: Hubertus Joannes Josephus Surinx, Genk, Belgium

[73] Assignee: Electro-Nite Co., Philadelphia, Pa.

[22] Filed: Sept. 26, 1974

[21] Appl. No.: 509,626

[30] Foreign Application Priority Data
Oct. 2, 1973  Luxemburg .................... 68549

[52] U.S. Cl. .................... 73/17 R; 73/354; 73/359; 73/DIG. 9
[51] Int. Cl.² .................................. G01N 25/04
[58] Field of Search ........ 73/17 R, 354, 359, DIG. 9

[56] References Cited
UNITED STATES PATENTS

| | | | |
|---|---|---|---|
| 3,267,732 | 8/1966 | Hance | 73/359 |
| 3,321,973 | 5/1967 | Anderson | 73/359 |
| 3,546,921 | 12/1970 | Bourk et al. | 73/17 |
| 3,559,452 | 2/1971 | Perbix et al. | 73/17 |
| 3,818,762 | 6/1974 | Kraus et al. | 73/359 |
| 3,844,172 | 10/1974 | Jeric | 73/354 |

OTHER PUBLICATIONS
"Carbon Equivalent in 60 Seconds" in Modern Castings Mar. 1962 pp. 37–39.
"Gray Cast Iron Control by Cooling Curve Techniques" p. 95 in Modern Castings Feb. 1962.

*Primary Examiner*—Herbert Goldstein
*Attorney, Agent, or Firm*—Seidel, Gonda & Goldhammer

[57] ABSTRACT

A disposable phase change device for sensing the rate of cooling of molten metal includes a body having a shallow elongated cavity on its upper surface. Sensing means extend across the cavity and is supported by first and second oppositely disposed walls on the body. The sensing means includes contacts adjacent opposite ends of the body. The upper surface of the body has one or more overflow cavities.

14 Claims, 4 Drawing Figures

U.S. Patent March 30, 1976 3,946,594
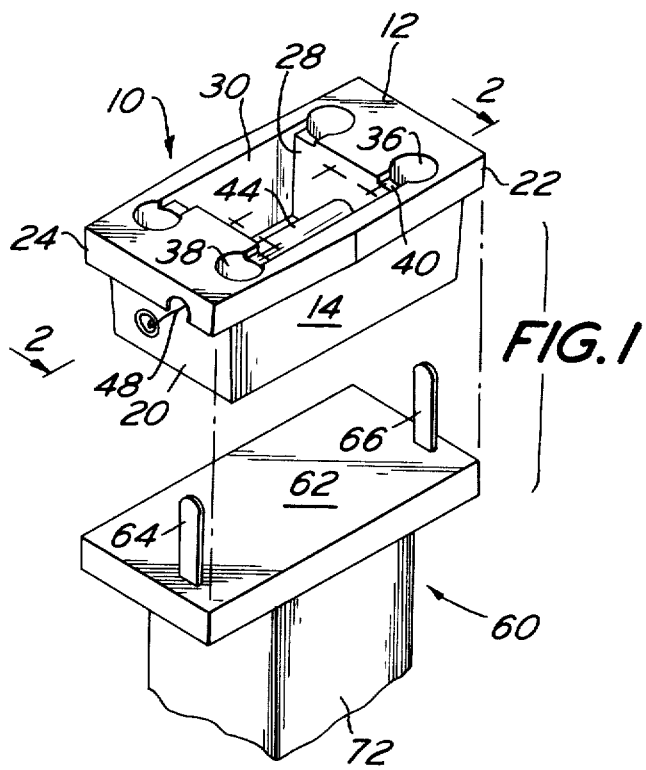
FIG.1
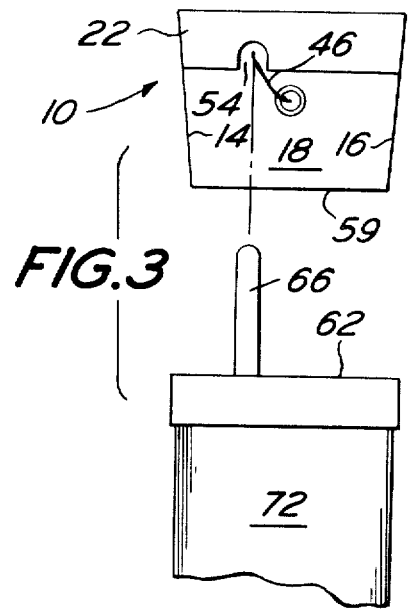
FIG.3
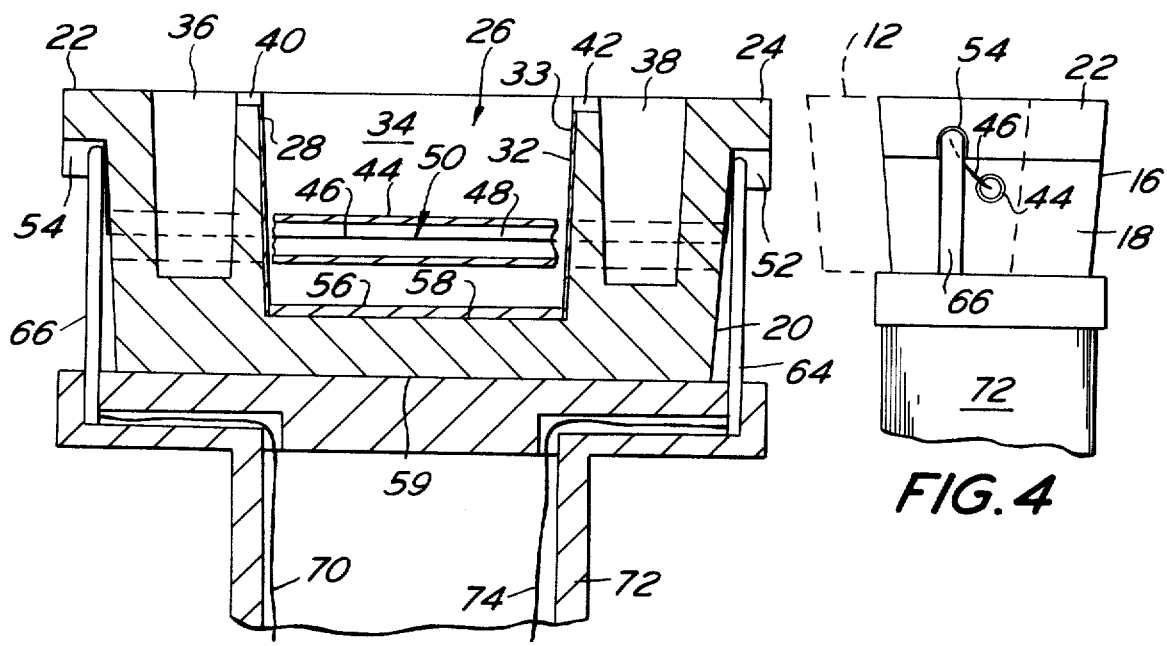
FIG.2
FIG.4

DISPOSABLE PHASE CHANGE DEVICE

BACKGROUND

This invention is directed to a disposable phase change device for sensing the rate of cooling of molten metal such as steel and cast iron. This invention is an improvement over prior art reflected by U.S. Pat. Nos. 3,611,808 and Re26,409.

While millions of devices as disclosed in said patents have been consumed, there are disadvantages resulting from the nature of the construction of said devices which are overcome by the present invention. The devices disclosed in said patents are upright cylinders and typically have an inner diameter of about 1¼ inches and a depth of about 2 inches. Thus, the target area for the operator when filling such cups is the cross sectional area of the cylinder. With an inner diameter of about 1¼ inches, the target area which must be filled by the operator is approximately 1.2 square inches. The present invention substantially increases the size of the target area so that it is easier for the operator to fill the device with molten metal. The present invention also takes into consideration the problem encountered when the operator overfills the device. Other problems associated with the prior art and advantages of the present invention are set forth hereinafter.

DISCLOSURE

The present invention is directed to a disposable phase change detector comprising a body having a shallow elongated cavity on its upper surface. The body is provided with a temperature sensing means for sensing the rate of cooling of molten metal in the cavity. The sensing means extends transversely across the cavity and is supported by first and second oppositely disposed walls of the body. The sensing means terminates in bare contacts adjacent opposite ends of the body.

In a preferred embodiment of the present invention, the body of the device is rectangular and has a flat bottom surface for maximizing the surface support area and minimizing any tendency of the body to tip over while being filled or after being filled with molten metal. The upper surface of the body preferably provided with at least one overflow cavity for receiving any excess molten metal introduced into the main cavity whereby such excess molten metal does not drip or flow down the outer sides of the body.

It is an object of the present invention to provide a low profile phase change detector structurally interrelated in a manner so as to have a mouth providing a large target area for introducing molten metal into the cavity and for rapid cooling of the molten metal while at the same time having a temperature sensing means of rapid response with electrical contacts which do not support the weight of the device and molten metal therein during use.

Other objects and advantages of the present invention will appear hereinafter.

For the purpose of illustrating the invention, there is shown in the drawings a form which is presently preferred; it being understood, however, that this invention is not limited to the precise arrangements and instrumentalities shown.

FIG. 1 is an exploded perspective view of a device in accordance with the present invention and its support stand.

FIG. 2 is a sectional view taken along the line 2—2 in FIG. 1 but on an enlarged scale.

FIG. 3 is an exploded end view of the device of the present invention and its support stand.

FIG. 4 is an end view showing the device mounted on its support stand.

Referring to the drawing in detail, wherein like numerals indicate like elements, there is shown in FIG. 1 a phase change detector device of the present invention designated generally as 10.

The device 10 includes a body designated generally as 12. The body 12 is a low flat body having upright elongated side walls 14 and 16 interconnected at their ends by end walls 18 and 20. A flange is provided so as to overlie each of the end walls. Thus, flange 22 projects beyond the end wall 18 while flange 24 projects beyond the end wall 20.

The body 12 is preferably cast or molded in one integral piece from a material which will withstand the temperatures of the molten metal to be introduced thereinto. Suitable materials for making the body 12 include sand having a resin binder, ceramics, coke, colloidal silicate dispersions, other refractory materials, etc.

The body 12 is formed with a main cavity 26 which is shallow and elongated. Cavity 26 is defined by upright wall surfaces 28, 30, 32 and 34. In connection with certain molten metals or in connection with ascertaining silicon content, it is desirable to ascertain the liquidus and solidus arrest temperatures. In that event, one or more of the walls of the cavity 26 have a coating 33 thereon. The coating 33 contains a carbide stabilizer which may be anyone of a wide variety of materials used heretofore in connection with hypereutectic or hypoeutectic cast iron. I prefer to use a wash containing tellurium as the coating 33 since tellurium is a very potent and inexpensive carbide stabilizer. Other stabilizers known to those skilled in the art include vanadium, lead, cerium, bismuth, etc.

The cavity 26 is preferably rectangular so as to maximize the target area to facilitate filling the cavity 26 with molten metal. The dimensions of the cavity 26 may be varied as desired. Suitable dimensions would include a length of 1¾ inches, a width of 1½ inches, and a depth of 1 inch. The volume of a cavity 26 having those dimension would be substantially equal to the volume of commercial embodiments of the devices set forth in said U.S. patents. At the same time, the mouth of the cavity 26 or target area is more than twice the target area of the upper end of said commercial embodiments of devices set forth in said patents.

Molten metal is usually poured from a ladle into the device 10. The size of the ladle is substantially larger than the size of device 10. In addition to providing a larger target area for the operator so that it would be easier to fill the cavity 26, the device 10 includes at least one overflow cavity on its upper surface. In the illustrated embodiment, two cavities 36 are provided at one end of the body 12 and two overflow cavities 38 are provided at the opposite end of the body 12. The number, shape and dimensions of said cavities 36, 38 may be varied as desired. Each cavity 36 communicates directly with the main cavity 26 by way of a passage 40. Each cavity 38 communicates with the main cavity 26 by way of a passage 42. If the operator pours too much molten metal into the cavity 26, it will overflow into the cavities 36, 38 rather than overflowing down the side of the body 12. Other advantages of cavities 36, 38 are set forth hereinafter.

A temperature sensing means is supported by the body 12 for sensing the rate of cooling of molten metal in the cavity 26 whereby a graph may be plotted indicative of the liquidus and solidus arrest temperatures of the specimen of molten metal within a short period of time. The temperature sensing means includes thermocouple wires 46 and 48 connected together at a hot junction 50 positioned at a location slightly below the midpoint of the height of the cavity 26. The wires 46 and 48 are preferably protected from direct contact with the molten metal to prevent a short circuit.

The structural interrelationship of the device 10 of the present invention facilitates using a protective means for preventing a short circuit between the thermocouple wires in the form of a straight length of tubing 44 made from a suitable protective material such as quartz, ceramic or other electrical nonconductive refractory material. The diameter of tubing 44 is sufficiently small so that heat is transmitted to the hot junction 50 by conduction and/or radiation.

The tubing 44 is supported at its ends by oppositely disposed walls on the body 12. The particular materials for the thermocouple wires 46 and 48 may vary depending upon the nature of the sample of molten metal introduced into the cavity 26. Where the sample is cast iron, thermocouple wire 46 may be of Chromel and wire 48 may be of Alumel. Where the sample is steel, wire 46 may be platinum and wire 48 platinum-rhodium.

As will be set forth in greater detail hereinafter, the body 12 is constructed so as to be supported independently of contacts associated with the thermocouple wires 46 and 48. Since the weight of the body 12 and any specimen therein is supported independently of the disposition of the thermocouple wires 46 and 48, these wires may be of substantially smaller diameter and thereby more rapidly responsive to the temperature of the specimen.

The flange 24 is provided with a recess 52 on its lower surface. The free end of wire 48 extends into the recess 52 and is a bare wire contact to be coupled to a recording instrument. Flange 22 is provided with a similar recess 54 on its lower surface. The free end of wire 46 extends into the recess 54 and is a bare wire contact for coupling to the recorder instrument. It will be noted that the recesses 52, 54 are offset with respect to the longitudinal axis of the tubing 44. While not necessary, this arrangement is preferred.

A metal chill plate 56 overlies the bottom wall 58 in the cavity 26. Chill plate 56 is optional and may be of any desired type of metal to facilitate a more rapid solidification of the specimen. Chill plate 56, when present, is trapped beneath the tubing 44 and hence need not be physically secured to the bottom wall 58 but if desired may be adhesively cemented thereto. The bottom wall 58 could be concave on its upper surface if desired.

The bottom surface 59 of the body 12 is a large flat surface occupying a space substantially greater than the cross sectional area of the cavity 26. The body 12 is adapted to be supported on a support stand 60 with the bottom surface 59 resting on a large flat surface 62. The weight of the body 12 and any specimen therein is supported on surface 62 by surface 59. When properly positioned on the surface 62, contact member 64 extends into the recess 52 and contacts the thermocouple wire 48. Likewise, contact member 66 extends into the recess 54 and contacts the thermocouple wire 46. As shown more clearly in FIG. 2, the end walls 18 and 20 of the body 12 are tapered upwardly. The distance across the end walls 18 and 20 at the location of the recesses 52 and 54 is slightly greater than the distance between the free upper ends of the contact members 64 and 66 to assure good mechanical and electrical contact.

The contact members 64 and 66 are connected to electrical conductors 70, 74 which extend downwardly through the support base 62 for connection to said recorder instrument. The materials for the contact members 64, 66 and the conductor 70 are chosen to be compatible with the thermocouple wires 46, 28 so that compensating materials are utilized where needed.

The contact members 64 are closer to one side edge of the platform 62. When the body 12 is properly located on the platform 62, the body 12 is in the solid line position shown in FIG. 4. If the body 12 is placed on the platform 62 in a manner so that contact member 64 is received within recess 54, the body 12 will be in the phantom position shown in FIG. 4 wherein it partially overhangs the side edge of the platform 62 and thereby clearly indicates to the operator that the device is improperly positioned.

The rectangular shallow cavity 26 presents a large target area for the operator filling the cavity 26 thereby making the device 10 easier and quicker to use. In addition, the large target area substantially increases the surface area for the molten metal introduced into the cavity 12 which accelerates the solidification of the molten metal. The chill plate 56, when used, will also accelerate the solidification of the molten metal. The flanges 22 and 24 prevent any molten metal from overflowing directly onto the thermocouple wires 46 and 48 while at the same time providing a convenient surface for contacting the body 12 and lifting the same off the platform 62 after a reading has been taken.

The cavities 36, 38 provide a means for retrieving a pin or chill-wedge sample of the specimen by using cavities of appropriate shape and dimensions. Hence, one of the cavities 36, 38 may be wedge shaped. The cavities 36, 38 also provide a means for obtaining uniformity in the amount of molten metal above the hot junction 50. This uniformity is important if it is desired to attain the same metalographic structure each time.

In view of the above description, those skilled in the art will not need a detailed explanation of the method in which the device 10 is used. Further, it will be obvious to those skilled in the art that the electrical contact members 64, 66 and the conductor 70 will be appropriately insulated from the metal portions of the support stand 60 so as to prevent short circuits.

The present invention may be embodied in other specific forms without departing from the spirit or essential attributes thereof and, accordingly, reference should be made to the appended claims, rather than to the foregoing specification as indicating the scope of the invention.

I claim:

1. A disposable phase change device comprising a body of refractory material having a shallow rectangular cavity open on its upper surface, the length of said cavity at its upper end being substantially greater than the depth of the cavity, temperature sensing means associated with said cavity for sensing the rate of cooling of molten metal in said cavity, said temperature sensing means extending transversely across said cavity, said sensing means having first and second end portions, each end portion being supported by a different one of oppositely disposed walls of said body, said body having at least one overflow cavity on its upper surface communicating with said first mentioned cavity, said body having a bottom surface constituting a support surface of the body, and said temperature sensing means terminating in contacts adjacent opposite ends of said body.

2. A device in accordance with claim 1 wherein said contacts are adjacent the upper end of said body, and said body having discrete recesses for receiving said contacts.

3. A device in accordance with claim 1 wherein said temperature sensing means includes thermocouple wires having a hot junction adjacent the center of the rectangular cavity and surrounded by a protector.

4. A device in accordance with claim 1 including a wash on at least one of the walls of said rectangular cavity, said wash containing a carbide stabilizer.

5. A device in accordance with claim 1 including a passage on said upper surface of said body, said passage providing communication between the upper ends of said rectangular cavity and said overflow cavity.

6. A disposable phase change detector comprising a body having a shallow elongated cavity on its upper surface into which a molten metal may be poured, said body and cavity being rectangular, the length of the cavity being greater than the depth of the cavity, a temperature sensing means for sensing the rate of cooling of molten metal in said cavity, said temperature sensing means extending substantially parallel to the upper surface of said body, said temperature sensing means including a straight hollow tubing with a thermocouple junction therein and protected thereby adjacent a central portion of the cavity with only one thermocouple wire extending through each end of said tubing, said tubing extending across the cavity with each end of the tubing being supported by a separate one of oppositely disposed walls of said body, said thermocouple wires having exposed contacts adjacent opposite ends of said body for coupling the same to a recording instrument, and said body having a flat bottom surface for supporting said body in a horizontal disposition.

7. A disposable phase change detector comprising a body having a main cavity on its upper surface into which molten metal may be directly poured, a temperature sensing means in said cavity at a location so that a sensing portion thereof will be surrounded by molten metal introduced into said cavity, means on said body for connecting said sensing means to an instrument, said body having a second cavity on its upper surface, said second cavity being smaller than said main cavity, means providing communication between the upper end portions of said cavities so that molten metal poured into said main cavity will overflow into said second cavity when the quantity of metal in said main cavity reaches a predetermined level, said main cavity having a length greater than its width in a horizontal plane, and a flat bottom surface on said body coextensive with the bottom wall of said main cavity for supporting said body in a horizontal disposition.

8. A device in accordance with claim 7 wherein said main cavity has one transverse dimension at its upper end which is substantially greater than the depth of said main cavity.

9. A device in accordance with claim 7 including a chill means in at least one of said cavities for chilling molten metal therein.

10. A disposable phase change detector comprising a body having a non-circular cavity defined by discrete walls, said cavity being exposed on the upper surface of said body and into which a molten metal may be directly poured, a temperature sensing means for sensing the rate of cooling the molten metal in said cavity, said temperature sensing means including a straight hollow tubing extending substantially parallel to the upper surface of said body with a thermocouple junction therein and protected thereby adjacent a central portion of the cavity with only one thermocouple wire extending through each end of said tubing, said tubing extending across the cavity with each end of the tubing being supported by a separate one of said walls of said body on opposite sides of said cavity, said thermocouple wires having exposed contact portions on an outer peripheral surface of said body for coupling the sensing means to a recording instrument, and at least a portion of said bottom surface of said body being flat and generally parallel to the longitudinal axis of said tubing for supporting said body in a position with said tubing being horizontally disposed.

11. A device in accordance with claim 10 wherein said body includes at least one overflow cavity on its upper surface and communicating with said first mentioned cavity.

12. A device in accordance with claim 10 including a carbide stabilizer in said cavity on a wall thereof.

13. A device in accordance with claim 10 including a metal chill plate in said cavity, and said body being a refractory material.

14. A disposable phase change detector comprising a rectangular body having a shallow elongated cavity on its upper surface in which a molten metal may be poured, the length of said cavity being greater than the depth of said cavity, a temperature sensing means for sensing the rate of cooling of molten metal in said cavity, said temperature sensing means extending substantially parallel to the length of said body, said temperature sensing means extending across the cavity, each end of said sensing means being supported by a separate one of oppositely disposed walls of said body, said sensing means including exposed contacts adjacent opposite ends of the body for coupling said sensing means to a recording instrument, said body having a flange projecting outwardly at said ends of said body, and a flat bottom surface on said body for supporting said body in a horizontal disposition.

* * * * *